United States Patent [19]

Kaiblinger

[11] Patent Number: 5,200,629
[45] Date of Patent: Apr. 6, 1993

[54] METHOD AND SYSTEM FOR CHANGING THE CONCENTRATION OF ONE MATERIAL IN A FLUID MEDIUM OF MIXED MATERIALS

[75] Inventor: Heinz J. Kaiblinger, Munich, Fed. Rep. of Germany

[73] Assignee: Chlean Plants & Engineering Establishment, Vaduz, Liechtenstein

[21] Appl. No.: 845,709

[22] Filed: Mar. 4, 1992

Related U.S. Application Data

[63] Continuation-in-part of Ser. No. 596,376, Oct. 12, 1990, Pat. No. 5,149,983.

[30] Foreign Application Priority Data

Mar. 5, 1991 [CH] Switzerland ............... 663/91

[51] Int. Cl.$^5$ .............. G01N 15/06; G01N 21/00
[52] U.S. Cl. ................ 250/575; 250/576; 356/438
[58] Field of Search ................ 250/573-576, 250/226; 356/437-440, 433, 435, 409, 307, 320; 422/83, 94, 102-104

[56] References Cited

U.S. PATENT DOCUMENTS

| | | | |
|---|---|---|---|
| 3,804,535 | 4/1974 | Rodriquez | 356/217 |
| 4,001,595 | 1/1977 | Reisman | 250/575 |
| 4,491,730 | 1/1985 | Pedersen | 356/433 |
| 4,539,296 | 9/1985 | Manabe | 436/47 |
| 4,641,973 | 2/1987 | Nestler et al. | 356/418 |
| 4,737,652 | 4/1988 | Faschingleitner et al. | 250/575 |
| 4,888,484 | 12/1989 | Harvey | 356/440 |
| 4,967,187 | 10/1990 | Dumas et al. | 356/438 |
| 5,002,391 | 3/1991 | Wolfrum et al. | 356/437 |
| 5,015,099 | 5/1991 | Nagai et al. | 356/437 |

Primary Examiner—David C. Nelms
Assistant Examiner—Michael Messinger
Attorney, Agent, or Firm—Brady, O'Boyle & Gates

[57] ABSTRACT

Radiations of two different frequencies are transmitted through a fluid comprising a mixture of materials, wherein a radiation is absorbed in the range of the radiation absorption by one of the materials, and another radiation is not absorbed, and wherein the radiations operate with pulses of identical pulse repetition frequency and identical pulse intervals. The detected electrical signal from the monitored radiations passed through the fluid, the center frequency of which corresponds to the reciprocal value of the pulse interval, is filtered out with the aid of a filter. The concentration of the absorbing material in the fluid is measured from the amplitude changes of the filtered-out signal. By the use of filters, the bandpass ranges of which are respectively adapted to the occurring pulse repetition frequencies, and based on the interpretation of the measuring signal as a modulated signal, a high safety against noise signals is attained. The measured concentration of the one material is then utilized by a combat circuit to add material into the mixture of fluid, which is constantly being monitored, to at least partly chemically connect the one material or another pollutant material in the fluid into another material to thus reduce the concentration of the same, with the process continuing whereby release of harmful chemicals into the atmosphere is progressively and continuingly diminished.

9 Claims, 3 Drawing Sheets

METHOD AND SYSTEM FOR CHANGING THE CONCENTRATION OF ONE MATERIAL IN A FLUID MEDIUM OF MIXED MATERIALS

This application is a continuation-in-part of my co-pending application Ser. No. 07/596,376, filed Oct. 12, 1990 now U.S. Pat. No. 5,149,983.

BACKGROUND OF THE INVENTION

The invention relates to a method and system for changing the concentration of at least one material in a fluid of mixed materials, such as changing the concentration of a pollutant substance in a flowing stream of fluid, having a mixture of substances or gases, such as, but not limited to exhaust gases from an internal combustion engine. The method and apparatus include measuring the concentration of one material or gas in the flowing stream of fluid and utilizing the measurements for injecting material into the flowing stream to at least partly chemically convert the one material or another material in the stream to thus reduce the concentration of the one or the other material or pollutant substance.

If a translucent medium is penetrated by radiation, the intensity of the transmitted radiation is dependent on the medium, the materials admixed to the medium, and the frequency of the radiation. From these frequency-dependent attenuation values, an unknown substance in the medium can be identified or, in case of a known substance, its concentration can be determined in the measuring path.

DOS 2,525,375 discloses a process of this type for measuring the concentration of materials. In the conventional method, the light beam of a semiconductor diode with tunable emission wavelength is passed through a measuring medium and detected. In order to determine the concentration of a gaseous component to be detected in the measuring medium, the emission wavelength is periodically switched over between the absorption maximum and an adjacent minimum. When the center frequency of the radiation emitted by the diode lies on the flank of the absorption line, the detector receives an alternating signal which is passed on to a phase-sensitive detector. The output signal of the latter is a direct measure for the concentration of the gaseous component in the measuring medium.

Another process of this type for measuring the concentration of materials has been known from DOS 3,741,026. In this method, a laser is switched to and fro between two of its inherent resonant frequencies, one of the resonant frequencies lying in the absorption maximum and the other resonant frequency lying in the absorption minimum of the gas to be detected. The concentration of the gas to be analyzed is derived from the relationship of the intensity attenuation of the two resonant frequencies. The value of the radiation intensity transmitted in each case is stored in a sample+hold circuit. The values stored in the sample+hold circuit are processed with a computer circuit at each measuring cycle.

Another process of this type for measuring the concentration of materials has been described in U.S. Pat. No. 3,804,535. In this process, a light source is utilized transmitting alternatingly light of two different frequencies; this light is passed through a measuring medium with a gas component, the concentration of which component is to be determined. The amplifier for the detection of the transmitted light for the two frequencies is turned on only during transmission of the light in order to thereby reduce signal noise in the received signal.

SUMMARY OF THE INVENTION

The present invention, as disclosed in the claims, describes a novel signal processing method wherein measurement of the concentration of a material contained in a measuring medium is performed by means of two differing radiations. The disclosed methods as well as their application are distinguished by a high protection effect from signal noise.

BRIEF DESCRIPTION OF THE DRAWINGS

Examples of the processes of this invention, of the apparatus of this invention, and its application will be described in greater detail below with reference to the drawings wherein.

DESCRIPTION OF THE PREFERRED EMBODIMENTS

Figure 1:
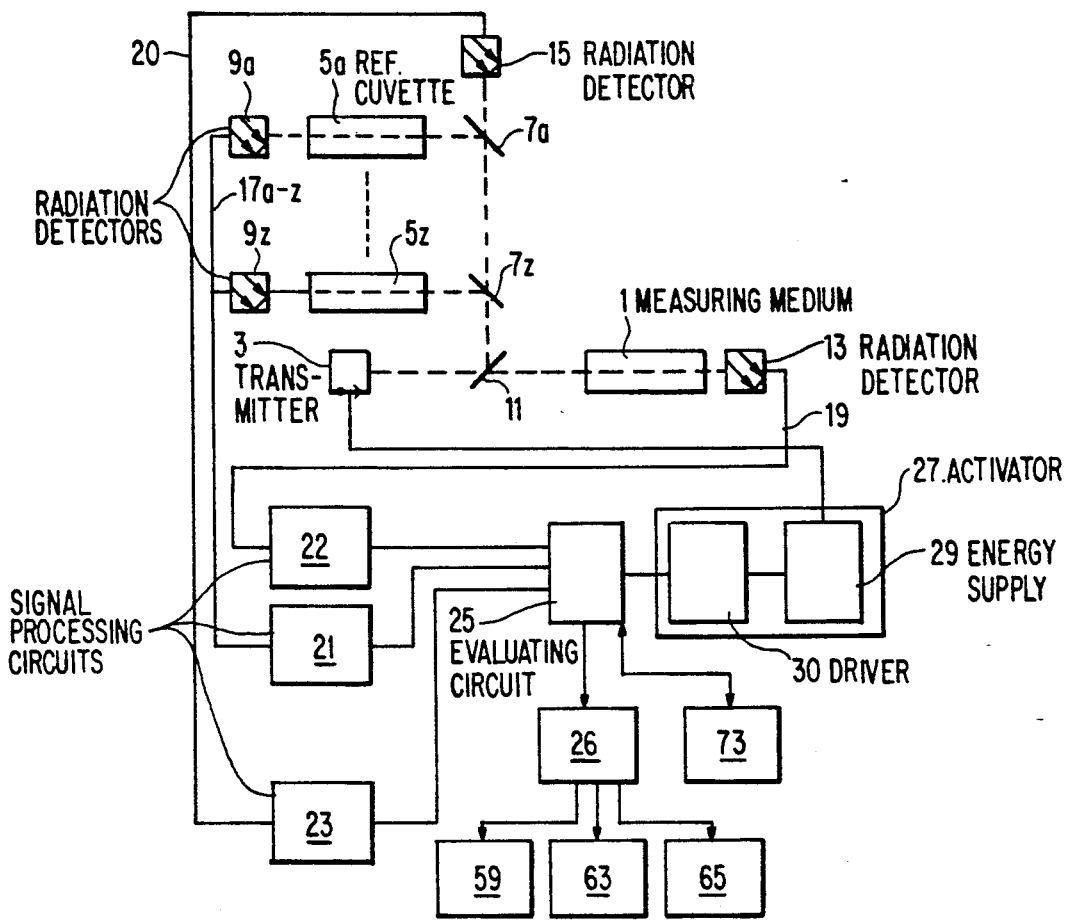
FIG. 1 is a block circuit diagram of an apparatus for the performance of concentration measurements.

The apparatus for measuring the concentration of materials in a measuring medium 1, illustrated in its block circuit diagram in FIG. 1, includes a transmitter 3, several measuring cuvettes $5a \ldots 5z$ each containing a reference medium with known absorption for the radiations transmitted by the transmitter 3 and of known concentration, with respectively one partially reflecting mirror $7a \ldots 7z$ and respectively one radiation detector $9a \ldots 9z$ which converts the radiation impinging thereon proportionally to the intensity into an electrical signal, with a further beam splitter 11 dividing the output radiation of the transmitter 3 into the measuring medium 1 and to the measuring cuvettes $5a \ldots 5z$, as well as with a detector 13 converting the intensity of the radiation transmitted through the measuring medium 1 into an electrical signal, and with a detector 15 on which impinges a portion of the radiation emitted by the transmitter 3 without having passed through a reference cuvette $5a \ldots 5z$ or the measuring medium 1. Each of the detectors $5a \ldots 5z$, 13, as well as 15 is connected by way of an electrical wire $17a \ldots 17z$, 19, and 20, respectively, with a signal processing circuit 21, 22 and 23, respectively. The signal processing circuits 21, 22 and 23 are connected to an evaluating circuit 25 determining the value of the concentration of the material contained in the measuring medium 1. The signal lines are indicated in FIG. 1 by solid lines, and the paths of radiation are shown in dashed lines.

Figure 2:
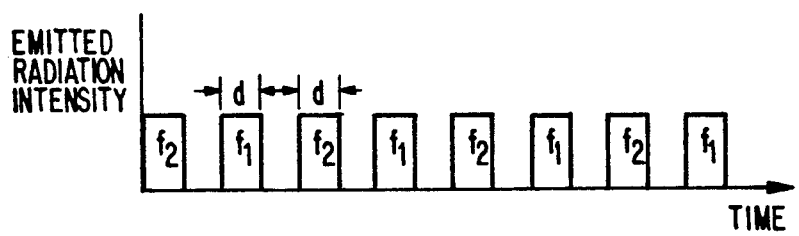
FIG. 2 shows the chronological sequence of the pulsed radiation transmitted by the transmitter of the apparatus, with the alternating frequencies $f_1$ and $f_2$.

The transmitter 3 is connected to an activator 27 containing an energy supply 29 and a driver 30. The driver 30 is a timer controlling the energy supply 29 in such a way that the transmitter 3 transmits pulses of differing radiations with the frequencies $f_1$ and $f_2$, with identical repetition frequency $1/T_N$ and constant pulse interval $T_T$ with respect to each other. The pulse interval $T_T$ is understood to mean the chronological distance from the pulse start of one pulse to the respective pulse start of the subsequent other pulse with the other radiation. Furthermore, the driver 30 is connected to the evaluating circuit 25 for synchronization of the measured value processing operation. The transmitter 3, as shown in FIG. 2, transmits pulsed radiation with a pulse width d having the frequencies $f_1$ and $f_2$. The pulse interval of pulses of identical radiation frequency $f_1$ or $f_2$ is $T_N$. The pulse interval $T_T$ of successive pulses has been chosen to be of equal size and amounts to half the pulse interval $T_N$. As seen from a frequency viewpoint, the frequency of all pulses is twice as large as the frequency of the pulses of a radiation frequency $f_1$ or $f_2$. Respectively one pulse with the frequency $f_1$ lies centrally between two pulses having the frequency $f_2$. Analogous remarks apply with regard to the pulses of frequency $f_2$.

When measuring the concentration of a known substance contained in the measuring medium 1 and in the reference cuvette 5a with a known concentration, a pulse having the pulse width d is transmitted by the transmitter 3 with a radiation of the radiation frequency $f_1$ lying in the range of the absorption maximum of the known substance. Several adjusting possibilities for the radiation frequencies $f_1$ and $f_2$ for varying transmitters 3 will be described below. This radiation $f_1$ impinges on the beam splitter 11 and is here divided. A portion of the radiation $f_1$ passes through the measuring medium 1; its intensity is measured by the detector 13, and the electrical measuring signal is passed on to the signal processing circuit 22. The other portion of the radiation $f_1$ impinges on the partially reflecting mirror 7a; the other partially reflecting mirrors . . . 7z are folded out of the way. At this mirror 7a, the radiation is once more divided. A portion of the radiation $f_1$ passes through the reference cuvette 5a. The thus-transmitted intensity is measured by the detector 9a, and the electrical measuring signal is passed on to the signal processing circuit 21. The residual portion of the radiation $f_1$ impinges on detector 15 and is passed on to the signal processing circuit 23.

Subsequently, the transmitter 3 is switched over and a pulse having the pulse width d with a radiation of the radiation frequency $f_2$ which the known material absorbs either not at all or only weakly, is transmitted analogously to the above procedure for frequency $f_1$. The entire above-described process is repeated.

Figure 3:
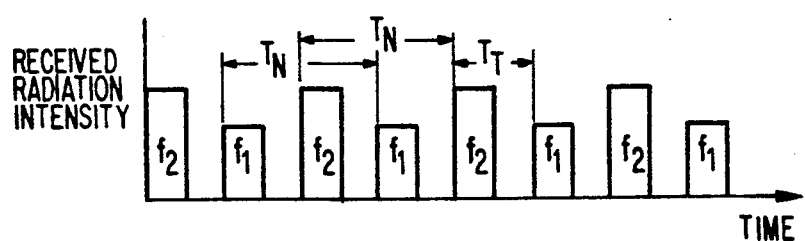
FIG. 3 shows a schematic view of the chronological sequence of the radiation illustrated in FIG. 2 after passing through the measuring medium and, respectively, the reference cuvette of the apparatus.

As shown in FIG. 2, the transmitter 3 transmits pulses having a constant and identical pulse repetition frequency $1/T_N$ and a constant pulse height. In alternation, a pulse having the radiation frequency $f_1$ and the subsequent pulse having the radiation frequency $f_2$ are transmitted. The intensity of the pulses having the radiation frequency $f_1$ is attenuated by the material in the measuring medium 1 and, respectively, in the reference cuvette 5a, and the intensity of the pulses having the radiation frequency $f_2$ is received by the detector 13 and, respectively, 9a in an almost non-attenuated fashion. The pulse train after leaving the transmitter 3 measured by the detector 15, is illustrated in FIG. 2. The pulse train after passing through the measuring medium 1, measured by detector 13, is shown in FIG. 3. The pulse trains passing through the reference cuvette 5a and the measuring medium 1 are similar to each other. FIG. 3 illustrates a typical pulse train schematically, as measured with detector 13. The pulse trains differ merely with respect to the absolute and relative values of the pulse heights. A measure for the concentration to be found is contained in the differing pulse heights.

Figure 4:
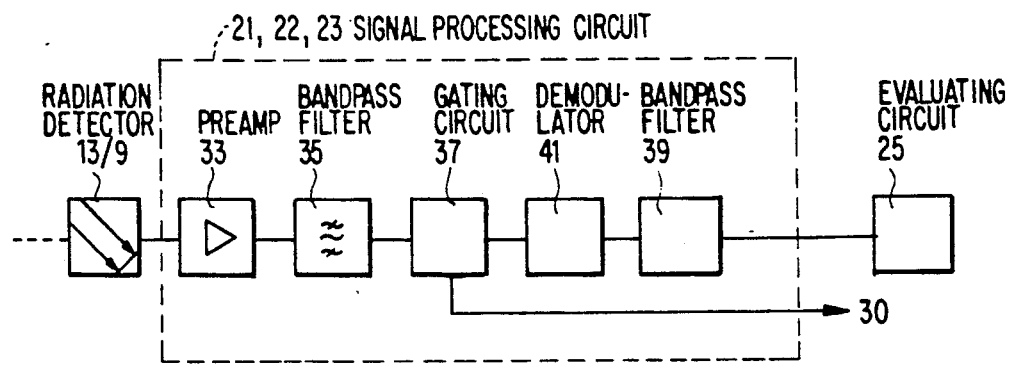
FIG. 4 is a block circuit diagram of the signal processing circuit of the apparatus.

In order to determine the sought-for concentration, the signals received by the detectors 9a, 13 and 15 are conducted into the signal processing circuits 21, 22 and 23, respectively. When using more than one reference cuvette 5a . . . 5z, as disclosed below, a changeover switch, not shown, is to be provided in front of the signal processing circuit 21 which selects the signal of the detectors 9a . . . 9z of the presently utilized reference cuvette 5a . . . 5z. The signal processing circuits 21, 22 and 23, respectively, comprise, in a series connection as shown in FIG. 4, a preamplifier 33, a filter 35, a chronological- and frequency-selective gating circuit 37 and 39, respectively, and a demodulator 41 for the electrical signal coming from detector 9a, 13 or 15. The chronological-selective gating circuit 37 is activated by the driver 30 in such a way that it allows only those signals to pass which appear at the point in time when pulses have been transmitted by the transmitter 3 and exhibit the same pulse form as the transmitted pulses. The filter 35 as a bandpass filter has a center frequency corresponding to the reciprocal value $1/T_T$ of the pulse interval $T_T$ of the pulses pertaining to radiation $f_1$ and $f_2$. In other words, the center frequency of the bandpass filter 35 is double the frequency of the pulse repetition frequency of the pulses having a frequency of $f_1$ and $f_2$, respectively. The output signal is passed on to the demodulator 41 for amplitude-modulated signals. The frequency-selective gating circuit as bandpass 39 has a center frequency corresponding to the reciprocal value $1/T_N$ of the pulse interval $T_N$ of the pulses of a radiation $f_1$ and $f_2$, respectively. The output signal of the bandpass 39 is fed to the evaluating circuit 25. The band-width of the bandpass 35 is adjusted so that the carrier frequency $1/T_N$ together with the information signal of the frequency $1/T_N$ will pass undamped. The band-width of the bandpass 39 with the center frequency $1/T_N$ is adjusted so that variations because of fluctuations of the concentration would pass without damping whereas thermal noise and short interruption because of dust passing the beam will have no influence on the information signal.

The signal received by the detector 9a is processed analogously to the above description and is likewise transmitted by the demodulator thereof (having analogous structure as demodulator 41) to the evaluating circuit 25. The difference of the signals passing via the lines is weighted with the known concentration in the reference cuvette 5a and yields the sought-for concentration in the measuring medium 1.

The electrical signal passing directly to the detector 15 is processed in an analogous fashion. The signal demodulated by the demodulator (designed analogously to demodulator 41) is, in the ideal case, a dc signal of the same height. However, since it is frequently impossible to produce the pulse heights of the pulses of frequencies $f_1$ and $f_2$ with identical pulse height, it is possible by convolution of this demodulated signal with the two other demodulated signals to again compensate for the differing pusle height of the pulses with differing frequencies $f_1$ and $f_2$. Also, the signal from detector 15 serves for monitoring the output power of the transmitter 3.

Figure 8:
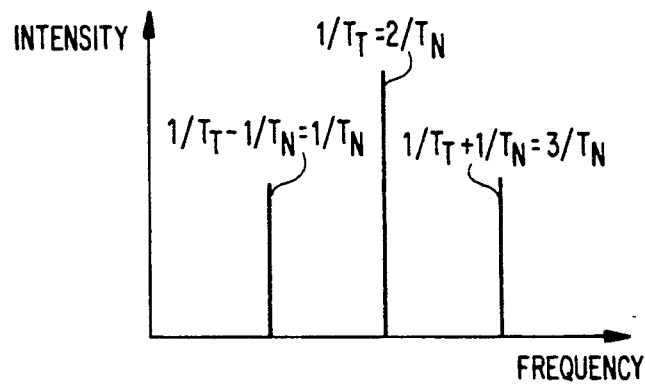
FIG. 8 shows a low-frequency frequency spectrum of the pulse sequence.

When observing the pulses received by the detectors 9a and 13, for example, with an oscilloscope, then a strongly noise-riddled image is obtained, the basic tendency of which is illustrated in FIG. 3. The radiation frequency $f_1$ and $f_2$ no longer plays any part with the electrical signals. This frequency is utilized further at this point merely for the identification of the varying transmitted pulses. When connecting a frequency analyzer in place of an oscilloscope, then a frequency $1/T_T$ appears besides a series of high frequencies, caused by the pulse shape; this frequency $1/T_T$ corresponds to the reciprocal value of the time interval $T_T$ of successive pulses of the first and second radiations $f_1$ and $f_2$. Also, to the left and to the right of this frequency value $1/T_T$, two further frequency values appear, as shown in FIG. 8, corresponding to the sum total and/or the difference of the frequency value $1/T_T$ and a frequency value corresponding to the reciprocal value of the time interval $T_T$ of the successive pulses of radiations $f_1$ and $f_2$. If then the concentration of the material in measuring medium 1 or in the reference cuvette is altered, the amplitude height of the frequency values $1/T_T + 1/T_N$ and $1/T_T - 1/T_N$ is altered in correspondence with the instanttaneous concentration. If, now, the pulses are transmitted by the transmitter 3, as described above, in such a way that the pulses have equal spacings from one another, then the frequency value $1/T_T - 1/T_N$ is half as large as the frequency value $1/T_T$, i.e. it is $1/T_N$. By the use of the bandpass 36 and the further bandpass 39 after the demodulator 41, a measurement can be performed which is approximately devoid of noise and interferences.

Figure 9:
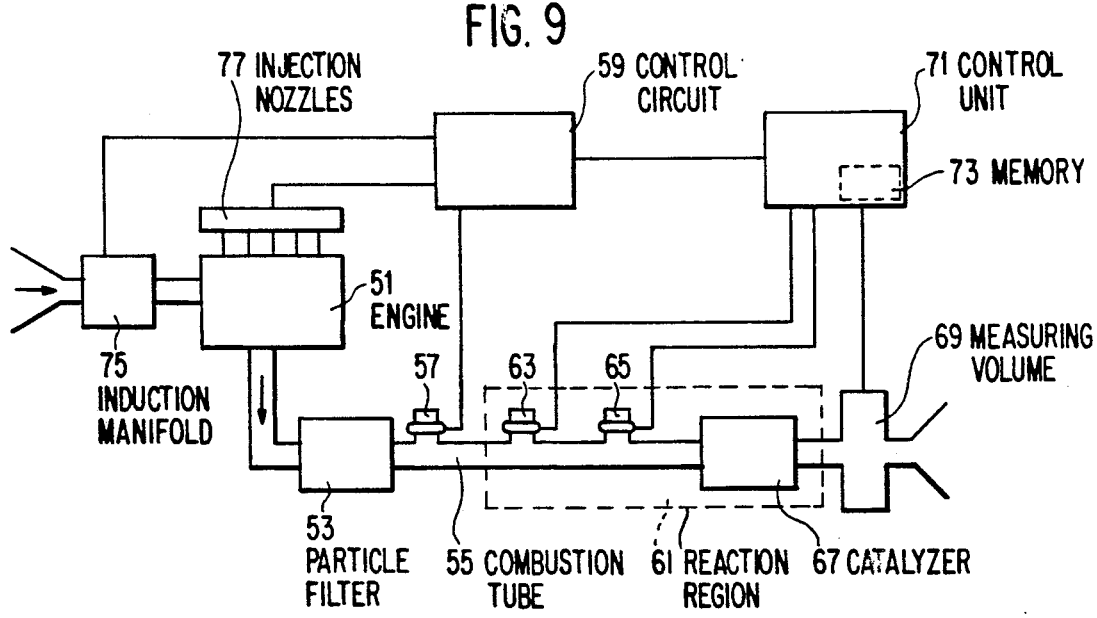
FIG. 9 is a schematic block diagram of the system of the invention connected for changing the concentration of pollutants in the exhaust gas of an internal combustion engine.

The above mentioned method for determining the concentration of at least one material within a fluid can be used in a method and system for denitrification (of $NO_X$) of a combustion gas of e.g. a diesel engine 51, as shown in FIG. 9.

After leaving the engine 51 by an exhaust pipe or combustion tube 55, the combustion gas flows through a particle filter 53, then passes a sensor 57 acting together with an engine control circuit 59. The sensor 57 measures the combustion gas pressure into the tube 55 for regulating e.g. a turbo engine, not shown. In the direction of the combustion gas flow, after the sensor 57, in the tube 55 there is a reaction region 61 of the system illustrated schematically by a dashed line surrounding the tube 55 in FIG. 9. The reaction region 61 comprises a first supply element 63 injecting fresh air and a second supply element 65 injecting ammonia into the combustion tube 55. After the reaction region 61, there is situated a catalyzer 67, followed by a measuring volume 69 corresponding to the measuring volume or measuring medium 1 used together with a control unit 71 for determining the concentration of ammonia within the combustion fluid. The control unit 71 comprises the above mentioned circuit of FIG. 1, and the components disclosed therein, such as several measuring cuvettes 5a ... 5z, the transmitter 3, partially reflecting mirrors 7a ... 7z and 11, radiation detectors 9a ... 9z, 13 and 15, signal processing circuits 21, 22 and 23, the evaluation circuit 25, the power driver 26 and the activator 27. The control unit 71 includes a memory 73 for data for adjusting the flow of ammonia and fresh air through the supply elements 63 and 65 into the reaction region 61 dependent on the measured concentration and to and for the data of the engine, such as the number of revolutions, sucked fresh air injected into the diesel, sucked and measured with an induction manifold 75, regulated by the engine control circuit 59, and quantity of fuel injected into the engine by an injection nozzle 77.

The chemical reaction occurring in the reaction region 61 is depicted by the well known equation

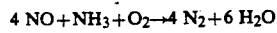

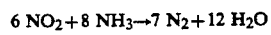

The measuring of the concentration is done continuously at about 500 Hz. With the results of the measurements and the data stored in the memory 73 the control unit 71 regulates the flow of ammonia through the supply element 65 and fresh air through supply element 63 in such a way that nearly all ammonia is reacted with the nitrogen oxides within the combustion gas in tube 55, and that therefore no ammonia will be emitted to the ambient atmosphere and the emission of NO and $NO_2$ will thus be as small as possible.

The inventive method for measuring the content of contamination or the combustion gas will also work with quick changement of the load of the diesel engine.

Instead of measuring the content of injected ammonia also the concentration of nitrogen oxides can be measured.

If the pulse width d is strongly reduced with respect to the pulse repetition frequency $1/T_N$, then the bandpass 35 is advantageously omitted, and a pulse amplitude demodulator is utilized as the demodulator 41.

Instead of using the gating circuit 37 merely as "window" which is opened solely when a pulse is expected, it is possible to effect in the gating circuit 37 a discrimination concerning the curve shape of the pulse to be received, which is not changed by the absorption in the measuring medium 1 or in the reference cuvette 5a.

Figure 5:
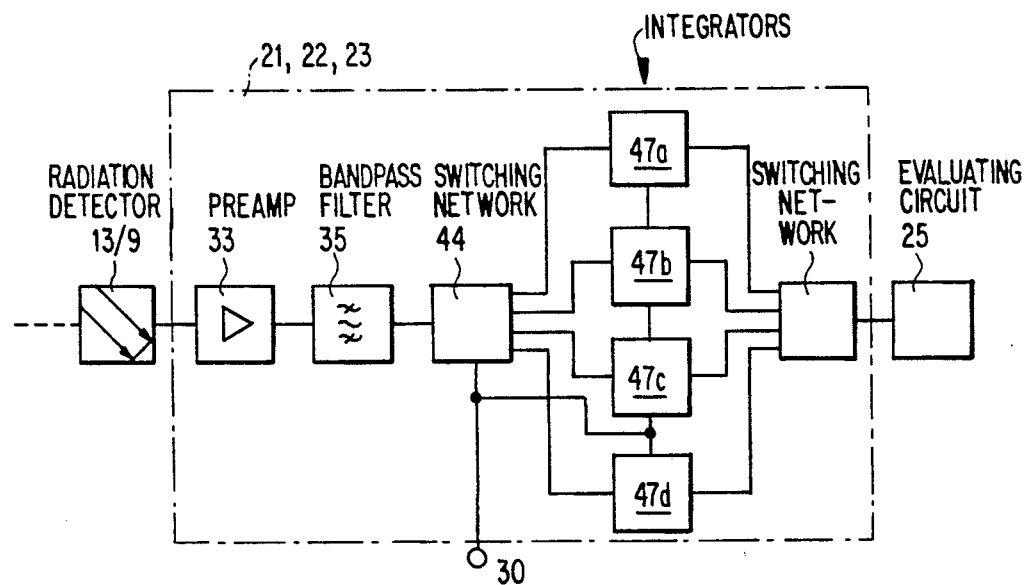
FIG. 5 shows a modification of the signal processing circuit illustrated in FIG. 4.
Figure 6:
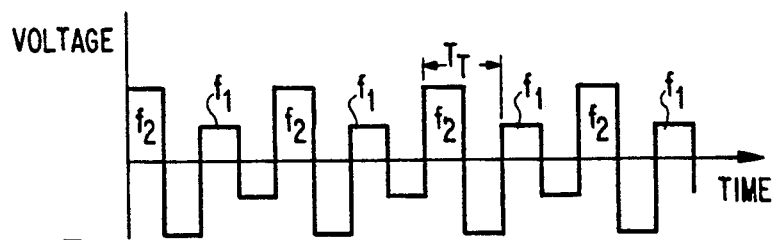
FIG. 6 is an idealized representation of the chronological pulse sequence shown in FIG. 3 after traveling through a bandpass of the signal processing circuit.

If small concentrations in the measuring medium 1 are involved in the analysis, then the signal detected by the detector 13 can be greatly noise-riddled. In this case, for optimum signal evaluation with the circuit shown in FIG. 5, the duration of the pulses is maximally adapted to the duration of the pauses between the pulses. The signal from detectors 9a ... 9z and 13 is introduced, after processing by means of amplifier 33 and filter 35, into a switching network 44 which passes the signals on to four subsequently connected integrators 47a to 47d in accordance with the control information from the driver 30. Since the integrals need not be determined at the same time but rather must all be available only at a predetermined point in time at the end of the measuring period, the integrals can be determined either via a single integrator with subsequently connected event switch or via the four integrators.

Respectively one integral $I_1$ and $I_2$ is formed for the time period during which a pulse is transmitted with radiation $f_1$ or $f_2$. Further integrals $I_3$ and $I_4$ are formed in the pulse-free time between the pulses with the radiation $f_1$ and $f_2$ and the pulses with the radiation $f_2$ and $f_1$. In the evaluation of the integrals, the value of integral $I_3$ is deducted from the value of integral $I_1$ in the evaluating circuit 25, and the thus-obtained electrical signal is set to zero prior to transmitting the pulse with radiation $f_2$. Subsequently, the value of integral $I_4$ is deducted from the value of integral $I_2$, and the electrical signal is likewise set at zero prior to transmission of the pulse with the radiation $f_1$. A thus-evaluated pulse train is illustrated over the time t as the abscissa in FIG. 7.

Figure 7:
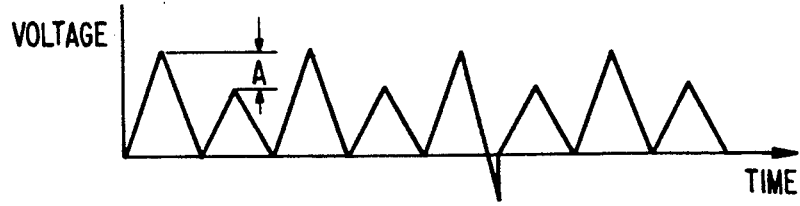
FIG. 7 shows an idealized representation of the chronological pulse sequence shown in FIG. 6 after passing through an integrator with discharge time constant of the signal processing circuit.

The sought-for concentration is derived from the difference values of the difference of the maximum integral values A for the signal of the detector 13 to the signal of detector 9a. Measuring disturbances occurring within the space of time when no signal should be present appear, as illustrated in FIG. 7, as a negative peak or as a positive step.

By forming, over each pulse, the integral and by effecting discharging in the subsequent pauses with a discharge time constant adjusted so that it discharges an integrated pulse with the radiation $f_1$ through the reference cuvette 5a again to just zero, then the electrical values prior to setting to zero yield a measure for the concentration.

In the above description, only the reference cuvette 5a is utilized, with a known concentration of a known material. In place of this single cuvette 5a, it is also possible to utilize z cuvettes with other materials of known concentrations. Depending on the material concentration to be measured, the partial beam of the transmitter 3 is conducted via the respective, partially reflecting mirror . . . 7z through the cuvette . . . 5z.

Suitable as the transmitter 3, transmitting at least two narrow-band radiations with a repetition frequency in the kilohertz range, are, inter alia, lasers, such as diode lasers, dye lasers, $CO_2$ lasers, two spectral lamps covered alternatingly by a revolving impeller wheel, etc. The lasers can be tuned to the two differing frequencies by pulsed excitation which takes place, for example, by electrical current, and by adjusting, between the pulses, for example, a grid or a resonator mirror in such a way that the laser oscillates at the respectively desired resonant frequency. It is also possible to utilize lamps, in front of which a fan wheel is rotating with filters separated from one another by nontransmitting regions. The transmission curves of the filters are selected so that they correspond to the above conditions. The number of revolutions of the filter wheel and the number of filter segments is chosen so that the resultant switchover frequency corresponds to the center frequency of the bandpass filter 35.

The absorption wavelengths of the materials, the concentration of which is to be determined in the measuring medium 1, are frequently in close proximity to one another; also, the absorption bandwidths are frequently very narrow. An exact adjustment of the radiation $f_1$ and $f_2$ can be obtained by passing the radiation of the transmitter 3 through the corresponding reference cuvette, filled with the respective material, and changing the frequency $f_1$ or $f_2$ of the transmitter 3 until the radiation lies within or, respectively, outside of the bandwidth of the absorption. It is also possible to arrange an automatic monitoring for the frequencies $f_1$ and $f_2$ to be adjusted.

When using, as the transmitters 3, lasers, especially solid lasers, dye lasers, $CO_2$ lasers, then the beam splitter mirror 11 can be omitted and instead it is possible to pass the one laser beam, exiting from one resonator mirror, into the measuring medium 1 and the other laser beam, exiting from the other resonator mirror, to the reference cuvettes 5.

The narrower the pulse width d is selected, the smaller can be the chosen "reception window" through which the gating circuit 37 transmits further a signal for continued processing. Interference pulses and false information can thereby likewise be reduced.

Instead of determining the concentration measurement by means of absorption of radiation in the measuring medium 1 and in the reference cuvette or cuvettes, it is also possible to take radiation scattering into account. In this case, the detector 13 is arranged beside the transmitter 3, and the detectors 9a . . . 9z are arranged in front of the reference cuvettes 5a . . . 5z in order to measure the intensity of the radiation scattered back from the measuring medium and/or from the respective reference cuvette. The pulse configuration of the backscattered pulses suffers "blurring" as compared with the transmitted pulse shape, but this need not be taken into account with the above-described measuring method insofar as the pulse transit time through the measuring medium 1 and the reference cuvette 5a . . . 5z is brief as compared with the pulse width d of the transmitted pulse.

By the use of filters, the passband of which is in each case adapted to the pulse repetition frequencies occurring, and due to the interpretation of the measuring signal as a modulated signal, a high security against noise signals is obtained.

Frequently, reagents are to be utilized which themselves are harmful to the environment, in the chemical conversion of materials, especially in the conversion of environmentally harmful pollutants into nonpolluting compounds or elements, present in varying, briefly fluctuating concentrations. Therefore, these reagents should be prevented from leaving the conversion process.

By a continuous determination of the exact quantities of the material to be converted at that particular time, it is made possible to admix an exact, chronologically dosable amount of reagents which, after having passed through the reaction zone, are either no longer present or are present only in a predetermined concentration.

Furthermore, by determining the exact quantity of the material to be converted, the amount of the material or the amount of the reagents can furthermore be adjusted so that, after traversal of the reaction zone, such an amount of the material and/or of the reagents is present that further processes can be performed, with or without concentration measurement, in additional reaction zones.

These methods are not only suitable for the elimination of materials harmful to the environment, but rather can also be utilized in the chemical industry for the manufacture of highly sensitive products, as well as for the conductance of chemical procedures wherein exactly meterable amount of materials and reagents must be employed.

The aforedescribed process is suitable, inter alia, for the performance of these chemical processes.

The method described herein can be utilized in the environmental protection field for the discovery of various pollutants. In particular, it is suitable for the control of waste gases in various industrial processes.

Ammonia ($NH_3$) can be used in the retransformation of nitrogen oxides formed, for example, in combustion processes into nitrogen and water. However, ammonia itself is a substance which pollutes the environment. Accordingly, ammonia must not be discharged into the atmosphere in chemical processes. By means of the method described above, it is now possible, for example, to determine with great accuracy the concentration of ammonia even in dynamic processes and to admix, by way of a regulation system, not shown, an amount of ammonia of exact quantity for purposes of retransformation.

The regulation is controlled via the concentration values determined by the evaluating circuit 25. These thus-determined concentration values are stored in the evaluating circuit 25 over an adjustable time span so that it is possible to transmit to the regulating system values even in such a case where the measuring signal fails for a short period of time, for example on account of dust within the beam in the measuring medium 1.

I claim:

1. A method for changing the concentration of at least another material within a fluid of mixed materials in a measuring medium (69) by determining the concentration of at least one material within the fluid in the measuring medium (69), wherein the at least one material is capable of at least partly chemically converting the at least another material, and the at least one material has a radiation frequency absorption range from an absorption maximum region to a low absorption region, comprising transmitting a first radiation having a frequency ($f_1$) in the range of the radiation absorption maximum of said material, and transmitting at least one second radiation with a frequency ($f_2$) lying in the low radiation absorption region of said material, along the same path through said measuring medium (69);

detecting the transmitted first and second radiations after passing through said measuring medium (69) by means of a detector (13) and converting the detected radiations into proportional electrical signals;

transmitting said first and second radiations $f_1$, $f_2$) in the transmitting step as pulses with the same constant repetition frequency ($1/T_N$) in alternating fashion;

maintaining the pulse intervals between the pulses of said first and said second radiations $f_1$, $f_2$) constant with respect to each other, and the time dependent intensity course of the pulses of said first and second radiations so as not to overlap each other;

dividing out a portion of the first and second radiations before entering said measuring medium;

placing a reference fluid containing a known concentration of said at least one material, the concentration of which is to be measured in said fluid in the measuring medium (69), in a reference volume (5a ... 5z);

passing the divided out portion of the first and second radiations through the reference volume (5a ... 5z) containing the reference fluid;

detecting the divided out portion of the first and second radiations after passing through said reference volume (5a ... 5z) and converting the detected radiations into proportional electrical signals;

demodulating said electrical signals from the detected first and second radiations passed through said measuring medium (69), and demodulating said electrical signals from the detected divided out portion of the first and second radiations passed through said reference volume (5a ... 5z;

integrating over a time span said electrical signals corresponding to the pulses of the first and second radiations $f^1$, $f_2$) passed through said measuring medium (69) and said electrical signals corresponding to the divided out portion of the first and second radiations passed through said reference volume (5a ... 5z);

comparing the integrated values of said electrical signals of said pulses of said first and said second radiations $f_1$, $f_2$) with one another in an evaluating circuit and determining the concentration of the said at least one material in the fluid in the measuring medium (69);

determining in the evaluating circuit the quantity of said one material required to at least partly chemically convert the another material within the fluid in the measuring medium (69); and chronologically injecting a quantity of said one material into said fluid thereby at least partly chemically converting the another material.

2. A method according to claim 1, including
continuously flowing said fluid into and through the measuring medium (69); and
injecting said one material into the flowing fluid upstream of the measuring medium (69).

3. A method for changing the concentration of at least another material within a fluid of mixed materials in a measuring medium (69) by determining the concentration of at least one material within the fluid in the measuring medium (69), wherein the at least one material is capable of at least partly chemically converting the at least another material, and the at least one material has a radiation frequency absorption range from an absorption maximum region to a low absorption region, comprising transmitting a first radiation having a frequency ($f_1$) in the range of the radiation absorption maximum of said material, and transmitting at least one second radiation with a frequency ($f_2$) lying in the low radiation absorption region of said material, along the same path through said measuring medium (69);

detecting the transmitted first and second radiations after passing through said measuring medium (69) by means of a detector (13) and converting the detected radiations into proportional electrical signals;

transmitting said first and second radiations $f_1$, $f_2$) in the transmitting step as pulses with the same constant repetition frequency ($1/T_N$) in alternating fashion;

maintaining the pulse intervals between the pulses of said first and said second radiations $f_1$, $f_2$) constant with respect to each other, and the time dependent intensity course of the pulses of said first and second radiations so as not to overlap each other;

dividing out a portion of the first and second radiations before entering said measuring medium;

placing a reference fluid containing a known concentration of said at least one material, the concentration of which is to be measured in said fluid in the measuring medium (69), in a reference volume (5a ... 5z);

passing the divided out portion of the first and second radiations through the reference volume (5a ... 5z) containing the reference fluid;

detecting the divided out portion of the first and second radiations after passing through said reference volume (5a ... 5z) and converting the detected radiations into proportional electrical signals;

demodulating said electrical signals from the detected first and second radiations passed through said measuring medium (69), and demodulating said electrical signals from the detected divided out portion of the first and second radiations passed through said reference volume (5a ... 5z);

integrating over a time span said electrical signals corresponding to the pulses of the first and second radiations ($f^1$, $f_2$) passed through said measuring medium (69) and said electrical signals corresponding to the divided out portion of the first and second radiations passed through said reference volume (5a ... 5z);

comparing the integrated values of said electrical signals of said pulses of said first and said second radiations ($f_1$, $f_2$) with one another in an evaluating circuit and determining the concentration of the said at least one material in the fluid in the measuring medium (69);

determining in the evaluating circuit the quantity of said another material required to at least partly chemically convert the one material within the fluid in the measuring medium (69); and chronologically injecting a quantity of said another material into said fluid thereby at least partly chemically converting the one material.

4. A method according to claim 3, including
continuously flowing said fluid into and through the measuring medium (69); and
injecting said another material into the flowing fluid upstream of the measuring medium (69).

5. A system for changing the concentration of at least one material, especially a pollutant substance, within a fluid streaming through a tube, comprising
a measuring volume (69) connected in the downstream portion of the tube,
a transmitter (3) for transmitting at least two radiations $f_1$, $f_2$) of differing frequencies and positioned to direct said radiations through said measuring volume (69);
an activator (27) connected for activating said transmitter (3);
a driver (30) connected for activating said activator (27);
a detector (13) on the opposite side of said measuring volume from said transmitter for detecting the radiation intensity of said two radiations $f_1$, $f_2$) transmitted or scattered through the fluid in said measuring volume (69);
an evaluation unit (25) electrically connected to the output of said detector (13);
a demodulator connected between said detector and evaluation unit (25);
a bandpass filter connected between the demodulator and the evaluation unit (25);
said activator connected to activate said transmitter (3) to alternately transmit non-overlapping pulses of said differing frequency radiations $f_1$, $f_2$) of constant as well as identical repetition frequency ($1/T_T$);
said bandpass filter having a center frequency corresponding to at least one of the differential or summation of the reciprocal values of the time intervals between successive pulses of said first and second radiations and said repetition frequency of the pulses of said first and second radiations and said repetition frequency of the pulses of said first radiation;
at least one reference medium (5a ... 5z) containing said at least one material, the concentration of which is to be measured in said measuring volume;
beam splitter means connected between said transmitter (3) and said measuring volume (69) in the path of the at least two radiations ($f_1$, $f_2$) and operable to divert a portion of said at least two radiations through said reference medium (5a ... 5z);
second detector means (9a ... 9z) connected to detect the intensity of said portion of said at least two radiations exiting said reference medium (5a ... 5z);
second demodulator means connected between said second detector means and said evaluation unit (25);
second bandpass filter means connected between said second demodulator and said evaluation unit (25);
integrator circuit means (47a ... 47d) connected in circuit between said first mentioned bandpass filter, said second bandpass filter means, and said evaluation unit (25);
switching means connected between said driver (30) and said integrator circuit means and operable by said driver (30) to switch said integrator circuit means on and off;
said tube having a reaction region;
supply means connected on said tube in said reaction region and connected for control by said evaluation unit, for supplying a quantity of at least another material into said reaction region of said tube for chemically converting at least part of said one material into a third material.

6. A system according to claim 5, in which said measuring volume is connected to said tube downstream of the reaction region of said tube.

7. A system according to claim 5, including
an internal combustion engine;
said tube being an exhaust pipe of said internal combustion engine;
said supply means comprising at least first and second supply elements;
said first supply element connected for injecting ammonia into said reaction region of said tube,
said evaluation unit connected to contact said first supply element and the chronological flow of the injected ammonia by said first supply element;
said second supply element connected for injecting fresh air into said reaction region of said tube,
said evaluation united connect to control said second supply element and the flow of injected fresh air by said second supply element;
said first radiation having a frequency in the range of the radiation absorption maximum of said ammonia or nitrogen oxides, and
said second radiation having a frequency lying in the low radiation absorption range of said ammonia or nitrogen oxides.

8. A system according to claim 5, in which said second bandpass filter means having a center frequency corresponding to the reciprocal value of the chronological distance ($T_T$) between successive pulses of said first and second radiations.

9. A system according to claim 5, including memory means connected in said evaluation unit and operable to store the determined concentration values of said at least one material over a predetermined time period.

* * * * *